(12) United States Patent
Fellers et al.

(10) Patent No.: US 9,909,139 B2
(45) Date of Patent: Mar. 6, 2018

(54) PLANT GERMPLASM RESISTANT TO RNA VIRUSES

(71) Applicants: The United States of America as represented by the Secretary of Agriculture, Washington, DC (US); Kansas State University Research Foundation, Manhattan, KS (US)

(72) Inventors: John Fellers, Manhattan, KS (US); Harold N. Trick, Olsburg, KS (US); Luisa Cruz, Plant City, FL (US); Jessica Rupp, Manhattan, KS (US)

(73) Assignees: The United States of America, as represented by The Secretary of Agriculture, Washington, DC (US); Kansas State University Research Foundation, Manhattan, KS (US)

( * ) Notice: Subject to any disclaimer, the term of this patent is extended or adjusted under 35 U.S.C. 154(b) by 486 days.

(21) Appl. No.: 14/494,661

(22) Filed: Sep. 24, 2014

(65) Prior Publication Data

US 2015/0089686 A1    Mar. 26, 2015

Related U.S. Application Data

(60) Provisional application No. 61/882,116, filed on Sep. 25, 2013.

(51) Int. Cl.
*C12N 15/82*    (2006.01)
*C07K 14/415*    (2006.01)

(52) U.S. Cl.
CPC ........ *C12N 15/8283* (2013.01); *C07K 14/415* (2013.01); *C12N 15/8218* (2013.01)

(58) Field of Classification Search
None
See application file for complete search history.

(56) References Cited

U.S. PATENT DOCUMENTS 7,772,462 B2 *    8/2010   Jahn ..................... C07K 14/415
                                                              800/278

OTHER PUBLICATIONS

Sequence Accession B44452, dated Jun. 10, 1993, attached to office action.*
Sequence Accession M95818, dated Apr. 27, 1993, attached to office action.*

* cited by examiner

*Primary Examiner* — Elizabeth McElwain
(74) *Attorney, Agent, or Firm* — John D. Fado; Ariel L. Atkinson

(57) ABSTRACT

Disclosed is a dsRNA construct used to silencing specific eukaryotic translation initiation factor in plants to produce a plant resistant to viruses such as Potyviruses, Luteoviruses, and Furoviruses. More specifically, the plant would be resistant to viruses such as Wheat streak mosaic virus, Triticum mosaic virus, Soil bourne mosaic virus, or Barley yellow dwarf virus. Also disclosed are non-transgenic wheat plants having the genes for eIF(iso)4E-2 or eIF4G silenced.

12 Claims, 2 Drawing Sheets

PLANT GERMPLASM RESISTANT TO RNA VIRUSES

CROSS-REFERENCE TO RELATED APPLICATION

This present application claims priority under 35 U.S.C. § 119(e) to U.S. Provisional Ser. No. 61/882,116, which was filed on Sep. 25, 2013, and is hereby incorporated by reference.

FIELD OF THE INVENTION

The present invention is related to silencing specific eukaryotic translation initiation factors in plants to produce a plant resistant to viruses such as Potyviruses, Luteoviruses, and Furoviruses. More specifically, the plant would be resistant to viruses such as Wheat streak mosaic virus, Triticum mosaic virus, Soil bourne mosaic virus, or Barley yellow dwarf virus.

BACKGROUND OF INVENTION

Fire, et al. (U.S. Pat. No. 6,506,559) discloses a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) discloses a method to inhibit expression of a target gene in a cell, the method comprising introduction of a double stranded ribonucleic acid into the cell in an amount sufficient to inhibit expression of the target gene, wherein the RNA is a double-stranded molecule with a first ribonucleic acid strand consisting essentially of a ribonucleotide sequence which corresponds to a nucleotide sequence of the target gene and a second ribonucleic acid strand consisting essentially of a ribonucleotide sequence which is complementary to the nucleotide sequence of the target gene. Furthermore, the first and the second ribonucleotide strands are separately complementary strands that hybridize to each other to form the said double-stranded construct, and the double-stranded construct inhibits expression of the target gene.

To utilize RNA interference as a method to regulate gene expression for control, a specific essential gene needs to be targeted. Coordinated gene expression requires factors involved in transcription and translation. Translation initiation coordinates activities of several eukaryotic initiation factors (eIF) or proteins which are classically defined by their cytoplasmic location and ability to regulate the initiation phase of protein synthesis. One of these factors, the eIF4F complex involves the expression of two proteins EIF(iso)4E-2 and EIF4G.

Disclosed in Caranta et al. (U.S. Pat. No. 7,919,677) is a method to obtain Potyvirus resistant plants having mutations in an eIF4E translation factor region. Additionally, disclosed in Jahn et al. (U.S. Pat. No. 7,772,462) is silencing of translation initiation factor eIF4E from *Capsicum annuum* imparted virus resistance to transgenic plants. Given the interest and showing of viral resistance to poyviruses related to eIF4 region, there is a need in the art to determine whether targeting eIF(iso)4E-2 or eIF4G via RNA interference induces viral resistance in vial susceptible plants.

BRIEF DESCRIPTION OF THE DRAWINGS

The present invention together with the above and other objects and advantages may best be understood from the following detailed description of the embodiment of the invention illustrated in the drawings, wherein.

BRIEF DESCRIPTION OF THE SEQUENCES

Figure 1A:
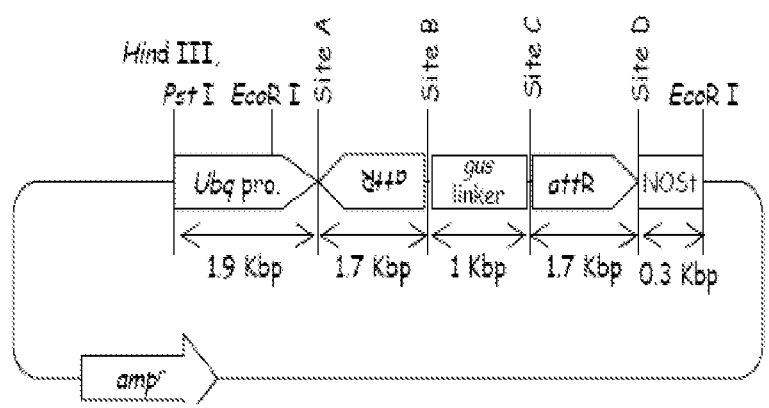
FIG. 1A and FIG. 1B depicts a vector map for a CP fragment cloned into pANDA mini vector by means of homologous recombination via LR clonase.

The invention can be more fully understood from the following detailed description and the accompanying sequence descriptions, which form a part of this application.

```
SEQ. ID. NO: 1:
ATGGCAGAGGTCGAAGCTGCGCTCCCGGTGGCGGCGACAGAGACCCCGGAGGTCGC

CGCCGAGGGCGACGCGGGTGCGGCCGAGGCGAAGGGGCCGCACAAGCTGCAGCGG

CAGTGGACCTTCTGGTACGACATCCAGACCAAGCCCAAGCCCGGCGCCGCCTGGGG

CACCTCGCTCAAAAAGGGCTACACCTTCGACACCGTCGAAGAGTTCTGGTGCTTGTA

TGATCAGATTTTCCGTCCGAGTAAGCTGGTAGGAAGTGCTGATTTTCATTTATTCAA

GGCTGGGGTAGAACCAAAGTGGGAAGATCCAGAGTGCGCAAATGGAGGCAAATGG

ACTGTGATATCTAGCAGGAAGACCAATCTTGATACCATGTGGCTTGAAACGTGTATG

GCTCTGATTGGAGAGCAGTTCGATGAAAGCCAGGAAATTTGTGGTGTTGTTGCTAGT

GTCCGCCAGAGACAGGATAAGCTTTCATTATGGACTAAGACTGCCAGTAACGAAGC

TGTTCAGGTGGACATTGGCAAGAAATGGAAGGAGGTTATTGACTACAATGATAAGA

TGGTCTACAGCTTCCACGATGACTCAAGAAGTCAGAAACCAAGCAGAGGTGGACGA

TACACCGTCTAA corresponds to the cDNA of eIF(iso)4E-2.

SEQ. ID. NO: 2:
MAEVEAALPVAATETPEVAAEGDAGAAEAKGPHKLQRQWTFWYDIQTKPKPGAAWG

TSLKKGYTFDTVEEFWCLYDQIFRPSKLVGSADFHLFKAGVEPKWEDPECANGGKWTV

ISSRKTNLDTMWLETCMALIGEQFDESQEICGVVASVRQRQDKLSLWTKTASNEAVQV
```

DIGKKWKEVIDYNDKMVYSFHDDSRSQKPSRGGRYTV corresponds to the amino acid sequence encoded by SEQ. ID. NO: 1.

SEQ. ID. NO: 3:
ATGGGGCATCAAGGACAAACCATGATGTATCCGTCTGTTGCTCATCCAATCCCTCCT
CAACTGGGCAATGTTAATTTGAACATGGCTTCACAGTATCCTCAGCAACAGCAGAAT
AAGCTTGTTGCTCCTCGAAAGAGCAGTAATATCAAAATTACTGATCCAAACACTAAC
AAAGAAGTGGTTCTTGGGCGGCCTTCACCTAATGTAGCAGTACAACCGCAGCAAGT
CAGTGGTGTTGCAACTCAGCCTATGGTTTACTATACTAATCCACAGCAGACCTCGTA
TAACCAGTCAGGCACGTATTACTCCGGCACTGCTGGTGTTGTTCCCACTGGATCACA
GGGCAGGTTTGGTTATCCTGCCACTCAAGCTGGTCAATCAATTCCTTTCATGAACCCT
TCTATGTCAAATACTGTTCCTGCCAGCCACAAGGACAACATAGCTGGGCCTGCACCA
TCTGGTCAGTCCCAACTCATAGGCAAACCACAAGGTGGGTTGCACATGGAGAAACC
TGTTCCCTCGGTCAAGATAAGTATGCCTGCAGGTAGATCAGACGCTTCTAAATTCGG
GGTCGCTGACCATGCGGTACAACATCGACAAAAGGATAATGAAGTTATTTCTGGTGC
TATGGTTTCGAATAAACCAGTTAGTGAGAAGGAGAGCAAGGCACCATCTATCCCAG
AGAAGCACTCCAAGGAAAGTAAAGCACCATCTGCCGTGGAGAAGCATCCCACTGCG
GTGACTCAACCTTTACCGATTCAAGCTGCAAAGCCAGAAACTGATGCAGCGACTGC
AAATTCACCCTCATTCTTGACCGGAGCTGATGAAAAGAAAGAATCCCTTCCAATGAC
TGATTCACTTAAGGATAACAAGAAAAATGCAACTAGAAATGACACAAAGAATTTGC
CGCAACAACCTCAGTCTGCTTCCCCTGCCGAAGAGTTGAAGGGGCAAACTTCTGTGA
AGCTTGGTGATGATGTGGTTGGTCACATGGAAACCAAGAGCTTCGATAGTGAAAAG
GTGGATTTAACCAGCAAGGTTTCAGGCTTAACATCAGCAACATCTGAAAGTAGTATT
TCTCCTATTCTTGGTAAAAGTGAAGCTGACAGCACATCAGTAGATGCTGCTGATGTT
CCTGCCATGGTAATCAGCTCTGCAAAATTGTCCTCTGCGAGCACTGGGGAGCCCCAA
GCAGTAGAAAGCTTAGGTGTTGCTGCTGTTAAATCTAAGGAGATTGAAATAACTCAC
CAAATTTCACCTGAATCTAGTGATGGCAAAATTATGTCTGATTCTACTGAAAATGAA
TCACATGACTTCACGGTGGACTTGGCTGAGCAGGCATCATTGGCAACTTCAAAGCCT
GGTAATTCAGATGCAACATCTTTTGTAACTGACCCGCAAGAGCTACCCAAGGAGTGC
ACAACATCTGTACCGGAGGACCACAGTTTGATGAATACATCACATAATAAGGATAC
CCAAACTTTATCAGCTTCTGTGGATGCCAGCGATGTGTCTGAGGTCAATTCTGGAAC
CTCATCAGAGTCTACCAGCCAAAGTACCAACGATAAAGATATCAGAAGTAGCATTC
AGGAAACTGGATTAGCTGTTTCTGGTATTACTCCTGGCATGTTGCCTGTGAATCATTC
AGTTGCATCTGAGGGGCAAGTCAAACATGCAGATGGAGCGAAGGATGAGTCTAGTA
CTGAGCAATCAAGTGCCGTACCAACAGGTTCTGTTAGACCCTTATCAAGGGAAAAA
CCTACTGCAGAGCTTGCCCGAACAAAGTCTACAGCTGGGAGAAAGAAGAAACGGAA
GGAAATGCTTTCAAAAGCTGATGCTGCTGGGAGCTCAGATCTGTACAATGCATACAA
AGGACCACAAGAACAGTCTGAGAGTGTTGCCACATCAGACGGTGCTGATAGTTCTTC
AACAGTCGACGGGACACATGTGCTGCCTGAGGAATCAGAAAGGGAGGTGATGTGTG
AGGACGATGGAAAGAAAAAAGTTGAGCCGGATGATTGGGAAGATGCAGCAGACAT
GTCTACTCCAAAGCTGCAAAGTTCGGACTCTGGAAACCAGGCTAGTGCAGTTCAATT
GCCAGATTCTGATATGACTGAAGCTAATGGCCGAAAGAAATATTCTCGTGATTTTCT

-continued

```
TCTAACTTTTGCACATCAGTATTCTAGTCTTCCTGTTGGCATCCGGATGGATACTGTC
ACTAGTACGCTATTCAAAGATTTGGCAGGAAAATCCTATGTTATTGATCGGGAACCT
CACCCAAGTTCTGCAAGGGGATCTGATAGACCAACATCTCGCGGTGATCGCCGTGGT
CCTGCTATGGATGATGATAAGTGGTTAAAATCAGGTGTTCCTTACAGTCCTAACCGT
GATGCCCACATGGACTTGACAAACGGCCCAGCAATTAATTACCGTGGCGGCCCAGG
AGGCGCTCATGGTGTTCTGAGGAATCCACGTGGTGCACTCCTTGTGGGACCACAATC
CAATGCTCCTCAAGTACCCCGCAGTGGCTCTGATGCAGATAGATGGCAGCAAAAGG
GTCTGATCCCATCTCCTGTTACACCCATGCAAGTAATGCACAAAGCCGAGAAAAAGT
ATGTTGTCGGCAAAGTTTCTGATGAGGAGCAGGCAAAGCAGAGGCAGCTGAAAGCC
ATTCTGAATAAACTGACCCCACAAAACTTTGACAAGCTTTTTGAACAAGTGAAAGAG
GTGAACATTGACAATGTATCAACTCTTACTGGGGTGATTTCACAGATATTTGACAAA
GCTTTGATGGAACCAACTTTCTGTGAAATGTATGCCAACTTCTGTTCCCATTTGGCTG
GTGCCCTGCCAGACTTTAGTGAGGACAATGAAAAGATTACATTCAAGAGACTGCTAT
TGAACAAGTGCCAAGAGGAGTTTGAGAGGGGAGAAAGAGAAGAAGCTGAAGCAGA
TAAAACGGAGGAGGAAGGTGAGATTAAGCAAACGAAAGAGGAAAGGGAAGAAAA
GAGAGTTAAAGCTCGAAGGCGCATGCTGGGTAATATTAGATTGATTGGAGAATTGT
ACAAAAAGAGGATGTTGACAGAGCGCATCATGCATGAATGCATCAAAAAATTGTTG
GGAAATTATCAGAATCCAGATGAGGAGAACATTGAAGCACTATGCAAATTGATGAG
TACAATTGGAGAGATGATAGATCATCCCAAGGCTAAGGAACATATGGATGCNTATT
TTGATAGAATGCGCAACCTGTCGACCAGTCAACTGATATCTTCCCGTGTTAGATTCC
TGCTCAGAGATTCAATCGATCTCAGGAAGAACAAATGGCAGCAAAGGCGTAAAGTG
GATGGCCCCAAGAAGATTGATGAGGTTCACAGGGATGCAGCTCAGGAAAGACATGC
TCAATCGAGTAGGTCTCGTGGTCCAGTCGTTAGTTCTCTTCCAAGAAGAGGGGCACC
CTCTATGGATTACGGCTCCCGTGGCTCAGCAGCACCATTGGTATCTCCAGGTCCTCA
GCAACGAGGGCGTGGATTTGGTAATCAAGATATTCGGTATGAGCAGGAAAGGCATC
AGTTTGATAGAACTGTTCCCCTTCCCCAGCGTTCTGTAAAGGACGAAGCTATCACTC
TTGGACCACAAGGTGGCCTAGCTAGGGGTATGTCTTTAAGAGGGCAGCCACCGGTA
TCAAATTCTGAACTTCCTAGTGTTGTTGACCAGCGCAGGATTGTATCTGGTCCTAATG
GGTACAATTCTGTGCCTTCAACAACAAGAGAAGACACTAGCTCTAGAATTCCAGATC
GATTTTCTGGGAGAATAGCACCTGCTGCACAATCTGCTAGTTCTTCACACAGACCTG
CCAGCCAGGAGGGTCGTTCAGGAAATAAATCATACTCTGAGGAGGAATTGAGAGAG
AAATCTATTGCAACCATCCGGGAATATTATAGTGCGAAAGATGAAAAGGAAGTTGC
ATTGTGTATTGAGGAGTTGAATGCTCCGAGCTTCTATCCTTCTCTTGTATCACTTTGG
GTAAATGATTCCTTTGAGAGGAAAGATATGGAAAGAGAGTTGTTGGCAAAGCTCTTT
GTCGGGCTTTACAATGGTGGATATAATTTATTGAGCAAGCCTCAGCTCATTGAGGGG
CTTTCATCCGTTCTTGCTTCATTGGAGGATGCTCTAAGTGATTCTCCAAGAGCGGCAG
AGTATCTTGGACGTCTTCTTGCAAGGTTTGTGGTGGAGAAGATACTGGTTTTGCAAG
ACGTAGGTAAATTGATTGAAGAAGGCGGAGAGGAGCCTGGACACCTTGTGCAGGAA
GGCATCGCAGCTGATGTCCTTGGCGCAGTCTTGGAGTGGATCAGAACAGAAAAGGG
GGATTCCTTCTTGAAGGAGGCCAAGACAAGCTCCAATCTCAAGTTGGAGGATTTCAG
```

-continued

ACCGCAGCATCTTAAGAGGTCAAAGTTGGATGCCTTCATGTTGACTTAA corresponds to the cDNA of eIF4G.

SEQ. ID. NO: 4:
MGHQGQTMMYPSVAHPIPPQLGNVNLNMASQYPQQQQNKLVAPRKSSNIKITDPNTNK

EVVLGRPSPNVAVQPQQVSGVATQPMVYYTNPQQTSYNQSGTYYSGTAGVVPTGSQG

RFGYPATQAGQSIPFMNPSMSNTVPASHKDNIAGPAPSGQSQLIGKPQGGLHMEKPVPS

VKISMPAGRSDASKFGVADHAVQHRQKDNEVISGAMVSNKPVSEKESKAPSIPEKHSKE

SKAPSAVEKHPTAVTQPLPIQAAKPETDAATANSPSFLTGADEKKESLPMTDSLKDNKK

NATRNDTKNLPQQPQSASPAEELKGQTSVKLGDDVVGHMETKSFDSEKVDLTSKVSGL

TSATSESSISPILGKSEADSTSVDAADVPAMVISSAKLSSASTGEPQAVESLGVAAVKSKE

IEITHQISPESSDGKIMSDSTENESHDFTVDLAEQASLATSKPGNSDATSFVTDPQELPKEC

TTSVPEDHSLMNTSHNKDTQTLSASVDASDVSEVNSGTSSESTSQSTNDKDIRSSIQETGL

AVSGITPGMLPVNHSVASEGQVKHADGAKDESSTEQSSAVPTGSVRPLSREKPTAELAR

TKSTAGRKKKRKEMLSKADAAGSSDLYNAYKGPQEQSESVATSDGADSSSTVDGTHVL

PEESEREVMCEDDGKKKVEPDDWEDAADMSTPKLQSSDSGNQASAVQLPDSDMTEAN

GRKKYSRDFLLTFAHQYSSLPVGIRMDTVTSTLFKDLAGKSYVIDREPHPSSARGSDRPT

SRGDRRGPAMDDDKWLKSGVPYSPNRDAHMDLTNGPAINYRGGPGGAHGVLRNPRG

ALLVGPQSNAPQVPRSGSDADRWQQKGLIPSPVTPMQVMHKAEKKYVVGKVSDEEQA

KQRQLKAILNKLTPQNFDKLFEQVKEVNIDNVSTLTGVISQIFDKALMEPTFCEMYANFC

SHLAGALPDFSEDNEKITFKRLLLNKCQEEFERGEREEAEADKTEEEGEIKQTKEEREEK

RVKARRRMLGNIRLIGELYKKRMLTERIMHECIKKLLGNYQNPDEENIEALCKLMSTIGE

MIDHPKAKEHMDAYFDRMRNLSTSQLISSRVRFLLRDSIDLRKNKWQQRRKVDGPKKI

DEVHRDAAQERHAQSSRSRGPVVSSLPRRGAPSMDYGSRGSAAPLVSPGPQQRGRGFG

NQDIRYEQERHQFDRTVPLPQRSVKDEAITLGPQGGLARGMSLRGQPPVSNSELPSVVD

QRRIVSGPNGYNSVPSTTREDTSSRIPDRFSGRIAPAAQSASSSHRPASQEGRSGNKSYSE

EELREKSIATIREYYSAKDEKEVALCIEELNAPSFYPSLVSLWVNDSFERKDMERELLAK

LFVGLYNGGYNLLSKPQLIEGLSSVLASLEDALSDSPRAAEYLGRLLARFVVEKILVLQD

VGKLIEEGGEEPGHLVQEGIAADVLGAVLEWIRTEKGDSFLKEAKTSSNLKLEDFRPQHL

KRSKLDAFMLT corresponds to the amino acid sequence encoded by

SEQ ID NO: 3.

SEQ. ID. NO: 5:
CACCCGCAAATGGAGGCAAATGGACTGT is a forward primer used to amplify a fragment of eIF(iso)4E-2.

SEQ. ID. NO: 6:
TCCACCTCTGCTTGGTTTCTGACT is a reverse primer used to amplify a fragment of eIF(iso)4E-2.

SEQ. ID. NO: 7:
CACCTCAGCAGCACCATTGGTATCTCCA is a forward primer used to amplify a fragment of eIF4G.

SEQ. ID. NO: 8
GCTCGGAGCATTCAACTCCTCAA is a reverse primer used to amplify a fragment of eIF4G.

DETAILED DESCRIPTION OF THE INVENTION

Disclosed herein is a method of producing a plant germplasm having resistance to RNA viruses, the method comprises introducing into a parental plant germplasm a chimeric DNA molecule comprising (i) a plant expressible promoter, (ii) a region which encodes dsRNA for eIF(iso)4E-2 or eIF4G which is capable of inhibiting RNA viral replication (iii) plant translation termination signal, b) transforming said parental plant germplasm, c) generating a plant germplasm from the parental plant germplasm comprising the chimeric DNA molecule; and d) selecting plant germplasm obtained from step (c) and identifying germplasm having immunity to viral RNA replication. In one embodiment of the invention, also disclosed is a transgenic plant produced by the method disclosed herein. In another embodiment of the invention, disclosed is a transgenic plant produced by the method disclosed where the plant is resistant to RNA plant viruses selected from the group consisting of Potyviruses, Luteoviruses, and Furoviruses. In yet another embodiment of the invention, disclosed is a transgenic plant produced by the method wherein the plant is resistant to Wheat streak mosaic virus. In yet another embodiment of the invention, disclosed is a transgenic plant produced by the method herein where the plant is resistant to Triticum mosaic virus. In yet another embodiment of the invention, disclosed is a transgenic plant produced by the method herein where the plant is resistant to Soil bourne mosaic virus. In another embodiment of the invention, disclosed is a transgenic plant produced by the method herein where the plant is resistant to Barley yellow dwarf virus.

In another embodiment of invention, the expression of transgenes and resistance phenotype remains stable in multiple generations of the progeny in the transgenic plant produced by the method herein. In another embodiment of the invention, the seed of a transgenic plant produced by the method herein.

In various embodiments of the invention, the method for transforming plant germplasm can be accomplish through a process selected from the group consisting of a biolistic particle delivery system, microprojectile bombardment, viral infection, *Agrobacterium*-mediated transformation, and electroporation.

In another embodiment of the invention, the method for producing a plant germplasm having resistance to RNA viruses is due to inhibited expression of an eIF(iso)4E-2 gene encoding a protein comprising SEQ. ID. NO: 2. In yet another embodiment of the invention, the method for producing a plant germplasm having resistance to RNA viruses is due to inhibited expression of an eIF4G gene encoding a protein comprising SEQ. ID. NO: 4. In another embodiment of the invention, disclosed is a transgenic plant having resistance to RNA viruses where said transgenic plant comprises a chimeric DNA molecule which encodes a double stranded RNA molecule for eIF(iso)4E-2 or eIF4G.

Disclosed herein is a nucleic acid construct comprising a nucleotide sequence of SEQ. ID. NO: 1 or an antisense sequence corresponding to SEQ. ID. NO: 1, wherein the construct is operably linked to a promoter that drives expression in a plant cell. Also disclosed is a vector comprising of the nucleic acid SEQ. ID. NO: 1. In an embodiment of the invention is a transgenic plant having stably incorporated in its genome the nucleotide sequence of SEQ. ID. NO:1.

Disclosed herein is a nucleic acid construct comprising of the nucleotide sequence of SEQ. ID. NO: 3 or an antisense sequence corresponding to SEQ. ID. NO: 3, wherein the construct is operably linked to a promoter that drives expression in a plant cell. Also disclosed is a vector comprising the nucleic acid SEQ. ID. NO: 3. In an embodiment of the invention is a transgenic plant having stably incorporated in its genome the nucleotide sequence of SEQ. ID. NO:3.

Disclosed herein is a non-transgenic plant comprising an eIF(iso)4E-2 allele in its genome, whereby the eIF(iso)4E-2 allele is an allele which encodes a protein comprising the amino acid sequence of SEQ. ID. NO: 1, characterized in that said eIF(iso)4E-2 allele comprises one or more mutations in its nucleotide sequence and whereby as a result of said one or more mutations the plant comprising said mutant allele in its genome has significant resistance to RNA viruses compared to a plant comprising a wild type eIF(iso)4E-2 allele in its genome. In an embodiment of the invention, disclosed is a non-transgenic plant produced by the method disclosed where the plant is resistant to RNA plant viruses selected from the group consisting of Potyviruses, Luteoviruses, and Furoviruses. In yet another embodiment of the invention, disclosed is a non-transgenic plant produced by the method wherein the plant is resistant to Wheat streak mosaic virus. In yet another embodiment of the invention, disclosed is a non-transgenic plant produced by the method herein where the plant is resistant to Triticum mosaic virus. In yet another embodiment of the invention, disclosed is a non-transgenic plant produced by the method herein where the plant is resistant to Soil bourne mosaic virus. In another embodiment of the invention, disclosed is a non-transgenic plant produced by the method herein where the plant is resistant to Barley yellow dwarf virus. In another embodiment of the invention, the seed of a non-transgenic plant produced by the method herein.

Disclosed is a non-transgenic plant comprising of an eIF4G allele in its genome, whereby the eIF4G allele is an allele which encodes a protein comprising the amino acid sequence of SEQ. ID. NO: 4, characterized in that said eIF4G allele comprises one or more mutations in its nucleotide sequence and whereby as a result of said one or more mutations the plant comprising said mutant allele in its genome has significant resistance to RNA viruses compared to a plant comprising a wild type eIF4G allele in its genome.

Definitions

To assist in the understanding of the invention, the following terms, as used herein, are defined below.

As used in the specification and claims, the singular form "a", "an" and "the" include plural references unless the context clearly dictates otherwise. For example, the term "a cell" includes a plurality of cells, including mixtures thereof.

The term "gene" refers to a DNA sequence involved in producing a polypeptide or precursor thereof. The polypeptide can be encoded by a full-length coding sequence or by any portion of the coding sequence, such as exon sequences. In one embodiment of the invention, the gene target is eIF(iso)4E-2 and eIF4G.

As used herein, the term "isolated" includes a material removed from its original environment, e.g., the natural environment if it is naturally occurring. For example, a naturally occurring polypeptide present in a living organism is not isolated, but the same polynucleotide or polypeptide, separated from some or all of the coexisting materials in the natural system, is isolated. Such polypeptide can be expressed by a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "double stranded RNA" or "dsRNA" refers to two substantially complementary strands of ribonucleic acid. "Identity," as used herein, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M Stockton Press, New York (1991)). Methods commonly employed to determine identity between sequences include, for example, those disclosed in Carillo, H., and Lipman, D., *SIAM J. Applied Math.* (1988) 48:1073. "Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a matrix for transcription. The target gene is therefore usually the sense strand.

The protein EIF(iso)4E-2 is also identified as eukaryotic translation initiation factor 4E-2, eIF-4E-2, eIF4E-2, eIF-(iso)4F, and eIF-(iso)4F p28 subunit.

The protein EIF4G is also identified as eukaryotic translation initiation factor 4G.

The term "complementary RNA strand" refers to the strand of the dsRNA, which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

As used herein, the term "recombinant DNA construct" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner using well-known recombinant DNA techniques.

A nucleic acid sequence can be inserted into a vector by a variety of procedures. In general, the sequence is ligated to the desired position in a vector following digestion of the insert and the vector with appropriate restriction endonucleases. Alternatively, blunt ends in both the insert and the vector may be ligated. A variety of cloning techniques are known in the art, e.g., as described in Sambrook, J. et al., *Molecular Cloning, A Laboratory Manual*, Cold Spring Harbor Press, Plainview, N.Y., (1989) and Ausubel, F. M. et al., Current Protocols in Molecular Biology, John Wiley & Sons, New York, N.Y. (1989). Such procedures and others are deemed to be within the scope of those skilled in the art.

The vector can be in the form of a plasmid, a viral particle, or a phage. Preferably, as disclosed herein the vector is a bacterial vector. Other vectors include chromosomal, non-chromosomal and synthetic DNA sequences, pET-30a and derivatives of pET-30; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook, T. et al., *Molecular Cloning: A Laboratory Manual*, Cold Spring Harbor Press, Plainview, N.Y., (1989).

"Small interfering RNA" or "siRNA" refers to a short double-strand of ribonucleic acid, approximately 18 to 30 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single strand of anti-sense ribonucleic acid and coupled with a protein complex named RISC. The antisense RNA then targets a complementary gene construct, such as messenger RNA that is cleaved by ribonuclease. While the examples infra discloses constructing dsRNA constructs via enzymatic techniques with the enzyme RNA polymerase, it is contemplated that siRNA can be constructed via RNA oligonucleotide synthesis such as those disclosed in Scaringe, S., Methods Enzymol., 2000, Vol. 317:3 and incorporated herein by reference.

As used herein, "knock-down" is defined as the act of binding an oligonucleotide with a complementary nucleotide sequence of a gene as such that the expression of the gene or mRNA transcript decreases. In an embodiment, knock-down of a eIF(iso)4E-2 and eIF4G gene in a transgenic plant confers resistance against viral RNA for said transgenic plant.

dsRNA containing a nucleotide sequence complementary to a portion of the eukaryotic translation initiation factor gene, preferably eIF(iso)4E-2 and eIF4G. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for plant resistance to RNA viruses. Thus, sequence identity may be optimized by sequence comparison and alignment algorithms known in the art. Thus, the determination of percent identity between any two sequences can be accomplished using a mathematical algorithm. Non-limiting examples of such mathematical algorithms are the algorithm of Myers and Miller (1988. CABIOS 4: 11-17), the local homology algorithm of Smith et al. (1981. Adv. Appl. Math. 2: 482); the homology alignment algorithm of Needleman and Wunsch (1970. J. Mol. Biol. 48: 443-453); the search-for-similarity-method of Pearson and Lipman (1988. Proc. Natl. Acad. Sci. 85: 2444-2448; the algorithm of Karlin and Altschul (1990. Proc. Natl. Acad. Sci. USA 87: 2264), modified as in Karlin and Altschul (1993. Proc. Natl. Acad. Sci. USA 90: 5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA), MacVector and Assembler Version 12.7 (Macvector. 1939 High House Road, Cary, N.C. USA 27519. Alignments using these programs can be performed using the default parameters.

Greater than 90% sequence identity, or even 100% sequence identity, between the inhibitory RNA and the portion of the eukaryotic translation initiation factor target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 18, 19, 21, 25, 50, 100, 200, 300, 400, 491, 500, or 510 bases. In a preferred embodiment, the length of the constructed double-stranded nucleotide sequence is approximately from about 18 to about 510 nucleotides in length.

The dsRNA construct disclosed herein may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell. Expression of higher doses of double-stranded construct may yield more effective RNA viral plant resistance.

While the examples provided wherein describe dsRNA constructs targeting eukaryotic initiation factor genes eIF (iso)4E-2 and eIF4G, (GenBank Accession Nos. Q03389 and EF190330), it is contemplated that when read in conjunction with the teaching disclosed herein, the construction of other dsRNA constructs targeting other eukaryotic initiation factor complex members which in turn reduce or eliminate viral reproduction and replication are disclosed herein.

Additionally it is contemplated that the disclosure herein would teach the transfer of a nucleic acid fragment into the genome of a host organism, resulting in genetically stable inheritance, particularly in a plant. Host organisms containing the transformed nucleic acid fragments are referred to as "transgenic" organisms. Examples of methods of plant transformation include *Agrobacterium*-mediated transformation (De Blaere et al. 1987. Meth. Enzymol. 143: 277) and biolistic particle delivery or "gene gun" transformation technology (Klein et al. 1987. Nature (London) 327: 70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transformation of plant cells or for the establishment of transgenic plants have been described in, e.g., Pouwels et al. 1985. Supp. 1987. Cloning Vectors: A Laboratory Manual; Weissbach and Weissbach. 1989. Methods for Plant Molecular Biology, Academic Press, New York; and Flevin et al. 1990. Plant Molecular Biology Manual, Kluwer Academic Publishers, Boston. Typically, plant expression vectors include, for example, one or more cloned plant genes under the transcriptional control of 5' and 3' regulatory sequences and a dominant selectable marker.

Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The teachings disclosed herein also teach generating a non-transgenic wheat plant having the genes for eIF(iso) 4E-2 or eIF4G silenced through the use of chemical mutagens such as ethyl methanesulfonate (EMS), radiation based mutagenesis such as fast neutron, or site directed mutagenesis, and targeted editing such as zinc finger nucleases, TALEN, or CRISPR technologies. An example would be to expose wheat seeds to 0.6% EMS. M0 seeds would be grown to maturity and allowed to self pollinate. Plants would be screened at the M2 generation for mutations in the eIF(iso)4E-2. DNA from lines would be pooled and TILLING would be used to identify mutant lines. Lines would be screened for resistance to WSMV and TriMV. Resistant lines would be used as germplasm for crop improvement. A second approach would be to use targeted mutations to alter the binding site of an initiation factor that binds to a binding protein to prevent interactions with viral proteins, thus preventing virus replication.

In an embodiment of the invention, targeted cleavage events can be used, for example, to induce targeted mutagenesis, induce targeted deletions of cellular DNA sequences, and facilitate targeted recombination and integration at a predetermined chromosomal ppTAC or ppeTAC locus. Techniques of nucleotide editing can be found for example, Urnov et al. (2010) Nature 435(7042):646-51; United States Patent Publications 20030232410; 20050208489; 20050026157; 20050064474; 20060188987; 20090263900; 20090117617; 20100047805; 20110207221; 20110301073; 2011089775; 20110239315; 20110145940; and International Publication WO 2007/014275, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) Proc. Natl. Acad, Sci. USA 104(9): 3055-3060 describes using designed ZFNs for targeted gene addition at a specified locus. U.S. Patent Publication 20110041195 describes methods of making homozygous diploid organisms.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

EXAMPLE 1: Cloning of eIF(iso)4E-2 (SEQ. ID. NO: 2)

A search term of "eIF4F" was used to identify a partial cDNA sequence from the TIGR wheat EST database (http:\jcvi.org\wheat\ wheat gene index term TC383303). That sequence was used in a BLASTX search to find the full length *Triticum aestivum* L. EIF(iso)4E-2 amino acid sequence in GenBank (Accession number Q03389). The nucleotide sequence of Q03389 was used to design the primers used to clone a portion of eIF(iso)4E-2. Forward CACCCGCAAATGGAGGCAAATGGACTGT (SEQ. ID. NO: 5) and Reverse TCCACCTCTGCTTGGTTTCTGACT (SEQ. ID. NO: 6) primers were used to amplify a 298 fragment of eIF(iso)4E-2 from cDNA from the cultivar Bobwhite corresponding to nucleotides 318-615.

CACC was added to the 5' end of the forward primer for directional cloning of the PCR fragment into the entry vector pENTER-D/TOPO (Life Technologies) which carries two recombination sites, attL1 and attL2. The CP fragment was independently cloned into pANDA mini vector (Miki and Shimamoto, 2003; FIG. 1A, FIG. 1B) by means of homologous recombination via LR clonase (Invitrogen, Carlsbad, Calif.).

EXAMPLE 2: Generation of Silenced eIF(Iso)4E-2 Transgenic Wheat Conferring Resistance to Viruses The construct was bombarded in five independent biolistic experiments using approximately 900 independent wheat embryos. Embryogenic calli was transferred into glufosinate selection and regeneration cycles, where morphological differentiation occurred normally. One hundred and nineteen plants were generated under glufosinate selection, and transferred to soil. Plants were tested for glufosinate resistance and 15 herbicide resistant plants were identified. PCR analyses of these plants identified three with the hairpin construct. Lines were self fertilized and tested in the T3 generation. The majority of the lines derived from single seed descent that contained the gene of interest (GOI) and were expressing were resistant to Wheat streak mosaic virus (WSMV) and Triticum Mosaic Virus (TriMV) both individually and during co-infection (Table 1). Seed from the $T_2$ generation were bulked for testing with Soilbourne mosaic virus (SbWMV). Soil infected with SbWMV was collected and used to grow plants. Most plants that had the GOI and were expressing the GOI were found to be resistant to the virus (Table 2). Bulked $T_2$ seed was also used for testing resistance to Barley yellow dwarf virus (BYDV). A viruliferous aphid colony containing three strains of BYDV, -SGV, -MAV and PAV were used. Ten viruliferous aphids were placed individually on each plant and allowed time to infect. Aphids were then destroyed. Plants were allowed to recover. Most plants that contained the GOI and were expressing were found to be resistant (Table 3).

TABLE 1

Transgenic wheat plant expressing silenced eIF(iso)4E-2 co-infected with WSMV and TriMV. Transgenic plants were T3 generation derived by single seed selection. Transgenic Bobwhite controls were lines expressing only the bar gene for biolophos resistance.

| T3 eIF4(iso)4E-2 | Total Plants | GOI + and Expressing | Resistant to WSMV | Resistant to TriMV |
|---|---|---|---|---|
| 1550A | 50 | 47 | 45 | 45 |
| 1822A | 53 | 45 | 40 | 40 |
| 1814A | 54 | 52 | 43 | 43 |
| Transgenic Bobwhite w/o GOI | 24 | 0 | 0 | 0 |

TABLE 2

Transgenic wheat plant expressing silenced eIF(iso)4E-2 infected with SbWMV. Transgenic plants were T3 generation bulk derived T2 progeny. Transgenic Bobwhite controls were lines expressing only the bar gene for biolophos resistance.

| T3 eIF4(iso)4E-2 | Total Plants | GOI + and Expressing | Resistant to SbWMV |
|---|---|---|---|
| 1550A | 75 | 32 | 26 |
| 1822A | 70 | 28 | 24 |
| 1814A | 73 | 30 | 24 |
| Transgenic Bobwhite w/o GOI | 17 | 0 | 0 |

TABLE 3

Transgenic wheat plant expressing silenced eIF(iso)4E-2 infected with BYDV. Transgenic plants were T3 generation bulk derived T2 progeny. Transgenic Bobwhite controls were lines expressing only the bar gene for biolophos resistance.

| T3 eIF4(iso)4E-2 | Total Plants | GOI + and Expressing | Resistant to BYDV |
|---|---|---|---|
| 1550A | 16 | 3 | 3 |
| 1822A | 10 | 7 | 6 |
| 1814A | 9 | 6 | 6 |
| Transgenic Bobwhite w/o GOI | 2 | 0 | 0 |

EXAMPLE 3: Cloning of eIF4G (SEQ: ID. NO. 4)

A search of "*Triticum aestivum* eIF4G" was used to identify the wheat eIF4G cDNA (EF190330) sequence from GenBank and used to design primers used to clone a portion of wheat eIF4G. The primers used were Forward CAC-CTCAGCAGCACCATTGGTATCTCCA (SEQ. ID. NO: 7) and Reverse GCTCGGAGCATTCAACTCCTCAA (SEQ. ID. NO: 8). The primers amplified a fragment of a 517 bp from regions 3479-3993 of the eIF4G sequence (EF190330). The fragment was amplified from cDNA from the cultivar Bobwhite.

Figure 1B:
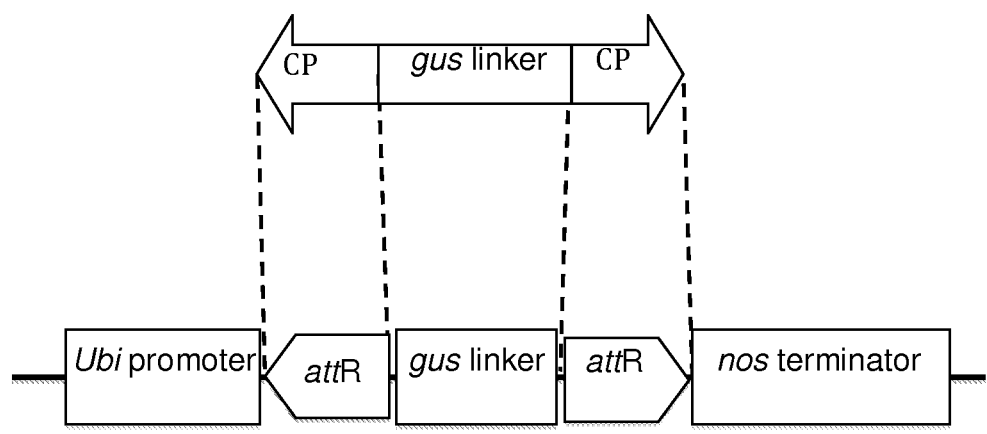

CACC was added to the 5' end of the forward primer for directional cloning of the PCR fragment into the entry vector pENTER-D/TOPO (Life Technologies) which carries two recombination sites, attL1 and attL2. The CP fragment was independently cloned into pANDA mini vector (Miki and Shimamoto, 2003; FIG. 1A, 1B) by means of homologous recombination via LR clonase (Invitrogen, Carlsbad, Calif.).

EXAMPLE 4: Generation of Silenced eIF4G Transgenic Wheat Conferring Resistance to Viruses A fragment of 517 bp from the host eukaryotic translation initiation factor G (GenBank Accession #EF190330.1) was cloned in pANDA mini and co-bombarded with pAHC20 in five independent biolistic experiments using approximately 900 wheat embryos. Embryogenic calli was transferred onto glufosinate selection. Seventy-two plants were generated under glufosinate selection and transferred to soil. PCR analyses confirmed the presence of the eIF4G hairpin construct in three lines of the bar-positive plants. Lines were self fertilized through the T3 generation. At the T3 generation, plants were inoculated with either WSMV or Triticum mosaic virus (TriMV) at the 2-3 leaf stage. Fourteen days later, plants were inoculated again to insure infection. Twenty-one days after the second inoculation, plants were scored for viral symptoms and compared to the nontransformed Bobwhite susceptible control. Leaf samples were also taken and used for ELISA to determine the presence of viral antigen. The majority of the lines that contained the gene of interest (GOI) were resistant to WSMV and TriMV both individually and during co-infection (Table 4). Seed from the $T_2$ generation were bulked for testing with Soilbourne mosaic virus (SbWMV). Soil infected with SbWMV was collected and used to grow plants. Most plants that had the GOI and were expressing the GOI were found to be resistant to the virus (Table 5). Bulked $T_2$ seed was also used for testing resistance to Barley yellow dwarf virus (BYDV). A viruliferous aphid colony containing three strains of BYDV, -SGV, -MAV and PAV were used. Ten viruliferous aphids were placed individually on each plant and allowed time to infect. Aphids were then destroyed. Plants were allowed to recover. Most plants that contained the GOI and were expressing were found to be resistant (Table 6). These results indicate the eIF4G hairpin construct provides resistance to the two potyviruses, the luteovirus and the furovirus.

TABLE 4

Transgenic wheat plant expressing silenced eIF4G co-infected with WSMV and TriMV. Transgenic plants were T3 generation derived by single seed selection. Transgenic Bobwhite controls were lines expressing only the bar gene for biolophos resistance.

| T3 eIF4G | Total Plants | GOI + and Expressing | Resistant to WSMV | Resistant to TriMV |
|---|---|---|---|---|
| 1673A | 50 | 47 | 47 | 47 |
| 1742A | 51 | 48 | 48 | 48 |
| 1755A | 50 | 48 | 48 | 48 |
| 1830A | 46 | 52 | 42 | 42 |
| Transgenic Bobwhite w/o GOI | 24 | 0 | 0 | 0 |

TABLE 5

Transgenic wheat plant expressing silenced eIF4G infected with SbWMV. Transgenic plants were T3 generation bulk derived T2 progeny. Transgenic Bobwhite controls were lines expressing only the bar gene for biolophos resistance.

| T3 eIF4G | Total Plants | GOI + and Expressing | Resistant to SbWMV |
|---|---|---|---|
| 1673A | 10 | 6 | 6 |
| 1742A | 29 | 19 | 15 |
| 1755A | 20 | 12 | 9 |
| 1830A | 12 | 7 | 7 |
| Transgenic Bobwhite w/o GOI | 11 | 0 | 0 |

TABLE 6

Transgenic wheat plant expressing silenced eIF4G infected with BYDV. Transgenic plants were T3 generation bulk derived T2 progeny. Transgenic Bobwhite controls were lines expressing only the bar gene for biolophos resistance.

| T3 eIF4G | Total Plants | GOI + and Expressing | Resistant to BYDV |
|---|---|---|---|
| 1673A | 10 | 4 | 3 |
| 1742A | 5 | 1 | 1 |
| 1755A | 7 | 2 | 2 |
| 1830A | 5 | 3 | 3 |
| Transgenic Bobwhite w/o GOI | 7 | 0 | 0 |

While the invention has been described with reference to details of the illustrated embodiment, these details are not intended to limit the scope of the invention as defined in the appended claims. All cited references and published patent applications cited in this application are incorporated herein by reference.

The embodiment of the invention in which exclusive property or privilege is claimed is defined as follows:

1. A method of producing a plant germplasm having resistance to RNA viruses, the method comprising:
   a) introducing into a parental plant germplasm a chimeric DNA molecule comprising (i) a plant expressible promoter, (ii) a region which encodes dsRNA for eIF(iso)4E-2 which is capable of inhibiting RNA viral replication, and (iii) a plant translation termination signal, b) transforming said parental plant germplasm, c) generating a plant germplasm from the parental plant germplasm comprising the chimeric DNA molecule; and d) selecting plant germplasm obtained from step (c) and identifying germplasm having immunity to viral RNA replication, wherein the plant germplasm is a wheat plant germplasm, and wherein said resistance is due to inhibited expression of a eIF(iso)4E-2 gene encoding a protein comprising SEQ. ID. NO: 2.

2. The plant germplasm produced by the method of claim 1.

3. The method of claim 1 wherein the plant is resistant to RNA plant viruses selected from the group consisting of Potyviruses, Luteoviruses, and Furoviruses.

4. The method of claim 1 wherein the plant is resistant to Wheat streak mosaic virus.

5. The method of claim 1 wherein the plant is resistant to *Triticum* mosaic virus.

6. The method of claim 1 wherein the plant is resistant to Soil bourne mosaic virus.

7. The method of claim 1 wherein the plant is resistant to Barley yellow dwarf virus.

8. The method of claim 1 wherein the expression of transgenes and resistance phenotype remains stable in multiple generations of the progeny.

9. The seed of a plant produced by the method of claim 1,
  wherein the seed has immunity to viral RNA replication, and
  wherein the seed comprises said chimeric DNA molecule.

10. The method of claim 1 wherein said transforming is through a process selected from the group consisting of a biolistic particle delivery system, microprojectile bombardment, viral infection, *Agrobacterium*-mediated transformation, and electroporation.

11. A transgenic wheat plant having resistance to RNA viruses, the transgenic wheat plant comprising a chimeric DNA molecule which encodes a double stranded RNA molecule for eIF(iso)4E-2,
  wherein the transgenic wheat plant is resistant to RNA viruses, and
  wherein said resistance is due to inhibited expression of a eIF(iso)4E-2 gene encoding a protein comprising SEQ. ID. NO: 2.

12. A transgenic wheat plant comprising a nucleotide sequence encoding the sequence of SEQ. ID. NO:1 or encoding the antisense sequence corresponding to SEQ. ID. NO:1, wherein said transgenic plant has increased resistance to positive strand RNA viruses.

* * * * *

SEQUENCE LISTING

<160> NUMBER OF SEQ ID NOS: 8

<210> SEQ ID NO 1
<211> LENGTH: 630
<212> TYPE: DNA
<213> ORGANISM: Triticum aestivum

<400> SEQUENCE: 1

```
atggcagagg tcgaagctgc gctcccggtg gcggcgacag agaccccgga ggtcgccgcc      60
gagggcgacg cgggtgcggc cgaggcgaag gggccgcaca agctgcagcg gcagtggacc     120
ttctggtacg acatccagac caagcccaag cccggcgccg cctggggcac ctcgctcaaa     180
aagggctaca ccttcgacac cgtcgaagag ttctggtgct tgtatgatca gattttccgt     240
ccgagtaagc tggtaggaag tgctgatttt catttattca aggctggggt agaaccaaag     300
tgggaagatc cagagtgcgc aaatggaggc aaatggactg tgatatctag caggaagacc     360
aatcttgata ccatgtggct tgaaacgtgt atggctctga ttggagagca gttcgatgaa     420
agccaggaaa tttgtggtgt tgttgctagt gtccgccaga gacaggataa gctttcatta     480
tggactaaga ctgccagtaa cgaagctgtt caggtggaca ttggcaagaa atggaaggag     540
gttattgact acaatgataa gatggtctac agcttccacg atgactcaag aagtcagaaa     600
ccaagcagag gtggacgata caccgtctaa                                      630
```

<210> SEQ ID NO 2
<211> LENGTH: 209
<212> TYPE: PRT
<213> ORGANISM: Triticum aestivum

<400> SEQUENCE: 2

```
Met Ala Glu Val Glu Ala Ala Leu Pro Val Ala Ala Thr Glu Thr Pro
  1               5                  10                  15

Glu Val Ala Ala Glu Gly Asp Ala Gly Ala Ala Glu Ala Lys Gly Pro
             20                  25                  30

His Lys Leu Gln Arg Gln Trp Thr Phe Trp Tyr Asp Ile Gln Thr Lys
         35                  40                  45

Pro Lys Pro Gly Ala Ala Trp Gly Thr Ser Leu Lys Lys Gly Tyr Thr
     50                  55                  60
```

```
Phe Asp Thr Val Glu Glu Phe Trp Cys Leu Tyr Asp Gln Ile Phe Arg
 65                  70                  75                  80

Pro Ser Lys Leu Val Gly Ser Ala Asp Phe His Leu Phe Lys Ala Gly
                 85                  90                  95

Val Glu Pro Lys Trp Glu Asp Pro Glu Cys Ala Asn Gly Gly Lys Trp
            100                 105                 110

Thr Val Ile Ser Ser Arg Lys Thr Asn Leu Asp Thr Met Trp Leu Glu
        115                 120                 125

Thr Cys Met Ala Leu Ile Gly Glu Gln Phe Asp Glu Ser Gln Glu Ile
    130                 135                 140

Cys Gly Val Val Ala Ser Val Arg Gln Arg Gln Asp Lys Leu Ser Leu
145                 150                 155                 160

Trp Thr Lys Thr Ala Ser Asn Glu Ala Val Gln Val Asp Ile Gly Lys
                165                 170                 175

Lys Trp Lys Glu Val Ile Asp Tyr Asn Asp Lys Met Val Tyr Ser Phe
            180                 185                 190

His Asp Asp Ser Arg Ser Gln Lys Pro Ser Arg Gly Gly Arg Tyr Thr
        195                 200                 205

Val

<210> SEQ ID NO 3
<211> LENGTH: 4467
<212> TYPE: DNA
<213> ORGANISM: Triticum aestivum
<220> FEATURE:
<221> NAME/KEY: misc_feature
<222> LOCATION: (3222)..(3222)
<223> OTHER INFORMATION: n is a, c, g, or t

<400> SEQUENCE: 3 atgggcatc aaggacaaac catgatgtat ccgtctgttg ctcatccaat ccctcctcaa     60
ctgggcaatg ttaatttgaa catggcttca cagtatcctc agcaacagca gaataagctt    120
gttgctcctc gaaagagcag taatatcaaa attactgatc aaacactaa caaagaagtg    180 gttcttgggc ggccttcacc taatgtagca gtacaaccgc agcaagtcag tggtgttgca    240
actcagccta tggtttacta ctactaatcca cagcagacct cgtataacca gtcaggcacg    300
tattactccg gcactgctgg tgttgttccc actggatcac agggcaggtt tggttatcct    360
gccactcaag ctggtcaatc aattcctttc atgaacccctt ctatgtcaaa tactgttcct    420
gccagccaca aggacaacat agctgggcct gcaccatctg tcagtccca actcataggc    480 aaaccacaag gtgggttgca catggagaaa cctgttccct cggtcaagat aagtatgcct    540
gcaggtagat cagacgcttc taaattcggg gtcgctgacc atgcggtaca acatcgacaa    600
aaggataatg aagttattc tggtgctatg gtttcgaata aaccagttag tgagaaggag    660
agcaaggcac catctatccc agagaagcac tccaaggaaa gtaaagcacc atctgccgtg    720
gagaagcatc ccactgcggt gactcaacct ttaccgattc aagctgcaaa gccagaaact    780
gatgcagcga ctgcaaattc accctcattc ttgaccggag ctgatgaaaa gaagaatcc    840 cttccaatga ctgattcact taaggataac aagaaaaatg caactagaaa tgacacaaag    900
aatttgccgc aacaacctca gtctgcttcc cctgccgaag agttgaaggg gcaaacttct    960
gtgaagcttg gtgatgatgt ggttggtcac atggaaacca agagcttcga tagtgaaaag   1020
gtggatttaa ccagcaaggt ttcaggctta acatcagcaa catctgaaag tagtatttct   1080
cctattcttg gtaaaagtga agctgacagc acatcagtag atgctgctga tgttcctgcc   1140
```

```
atggtaatca gctctgcaaa attgtcctct gcgagcactg gggagcccca agcagtagaa    1200
agcttaggtg ttgctgctgt taaatctaag gagattgaaa taactcacca aatttcacct    1260
gaatctagtg atggcaaaat tatgtctgat tctactgaaa atgaatcaca tgacttcacg    1320
gtggacttgg ctgagcaggc atcattggca acttcaaagc ctggtaattc agatgcaaca    1380
tcttttgtaa ctgacccgca agagctaccc aaggagtgca acatctgt accggaggac     1440 cacagtttga tgaatacatc acataataag gatacccaaa ctttatcagc ttctgtggat    1500
gccagcgatg tgtctgaggt caattctgga acctcatcag agtctaccag ccaaagtacc    1560
aacgataaag atatcagaag tagcattcag gaaactggat tagctgtttc tggtattact    1620
cctggcatgt tgcctgtgaa tcattcagtt gcatctgagg ggcaagtcaa acatgcagat    1680
ggagcgaagg atgagtctag tactgagcaa tcaagtgccg taccaacagg ttctgttaga    1740
cccttatcaa gggaaaaacc tactgcagag cttgcccgaa caaagtctac agctgggaga    1800
aagaagaaac ggaaggaaat gctttcaaaa gctgatgctg ctgggagctc agatctgtac    1860
aatgcataca aaggaccaca agaacagtct gagagtgttg ccacatcaga cggtgctgat    1920
agttcttcaa cagtcgacgg gacacatgtg ctgcctgagg aatcagaaag ggaggtgatg    1980
tgtgaggacg atggaaagaa aaaagttgag ccggatgatt gggaagatgc agcagacatg    2040
tctactccaa agctgcaaag ttcggactct ggaaaccagg ctagtgcagt tcaattgcca    2100
gattctgata tgactgaagc taatggccga agaaatatt ctcgtgattt tcttctaact      2160
tttgcacatc agtattctag tcttcctgtt ggcatccgga tggatactgt cactagtacg    2220
ctattcaaag atttggcagg aaaatcctat gttattgatc gggaacctca cccaagttct    2280
gcaaggggat ctgatagacc aacatctcgc ggtgatcgcc gtggtcctgc tatggatgat    2340
gataagtggt taaaatcagg tgttccttac agtcctaacc gtgatgccca catggacttg    2400
acaaacggcc cagcaattaa ttaccgtggc ggcccaggag cgctcatgg tgttctgagg      2460 aatccacgtg gtgcactcct tgtgggacca caatccaatg ctcctcaagt accccgcagt    2520
ggctctgatg cagatagatg cagcaaaaag ggtctgatcc catctcctgt tacacccatg    2580
caagtaatgc acaaagccga gaaaaagtat gttgtcggca aagttctga tgaggagcag     2640 gcaaagcaga ggcagctgaa agccattctg aataaactga ccccacaaaa ctttgacaag    2700 cttttttgaac aagtgaaaga ggtgaacatt gacaatgtat caactcttac tggggtgatt    2760
tcacagatat ttgacaaagc tttgatggaa ccaactttct gtgaaatgta tgccaacttc    2820
tgttcccatt tggctggtgc cctgccagac tttagtgagg acaatgaaaa gattacattc    2880
aagagactgc tattgaacaa gtgccaagag gagtttgaga ggggagaaag agaagaagct    2940
gaagcagata aaacggagga ggaaggtgag attaagcaaa cgaaagagga agggaagaa     3000 aagagagtta agctcgaagg cgcatgctg gtaatatta gattgattgg agaattgtac      3060
aaaaagagga tgttgacaga gcgcatcatg catgaatgca tcaaaaaatt gttgggaaat    3120
tatcagaatc cagatgagga gaacattgaa gcactatgca aattgatgag tacaattgga    3180
gagatgatag atcatcccaa ggctaaggaa catatggatg cntattttga tagaatgcgc    3240
aacctgtcga ccagtcaact gatatcttcc cgtgttagat tcctgctcag agattcaatc    3300
gatctcagga agaacaaatg gcagcaaagg cgtaaagtgg atggccccaa gaagattgat    3360
gaggttcaca gggatgcagc tcaggaaaga catgctcaat cgagtaggtc tcgtggtcca    3420
gtcgttagtt ctcttccaag aagaggggca ccctctatgg attacggctc ccgtggctca    3480
gcagcaccat tggtatctcc aggtcctcag caacgagggc gtggatttgg taatcaagat    3540
```

```
attcggtatg agcaggaaag gcatcagttt gatagaactg ttccccttcc ccagcgttct   3600
gtaaaggacg aagctatcac tcttggacca caaggtggcc tagctagggg tatgtcttta   3660
agagggcagc caccggtatc aaattctgaa cttcctagtg ttgttgacca gcgcaggatt   3720
gtatctggtc ctaatgggta caattctgtg ccttcaacaa caagagaaga cactagctct   3780
agaattccag atcgattttc tgggagaata gcacctgctg cacaatctgc tagttcttca   3840
cacagacctg ccagccagga gggtcgttca ggaaataaat catactctga ggaggaattg   3900
agagagaaat ctattgcaac catccgggaa tattatagtg cgaaagatga aaaggaagtt   3960
gcattgtgta ttgaggagtt gaatgctccg agcttctatc cttctcttgt atcactttgg   4020
gtaaatgatt cctttgagag gaaagatatg gaaagagagt tgttggcaaa gctctttgtc   4080
gggctttaca atggtggata taatttattg agcaagcctc agctcattga ggggctttca   4140
tccgttcttg cttcattgga ggatgctcta agtgattctc caagagcggc agagtatctt   4200
ggacgtcttc ttgcaaggtt tgtggtggag aagatactgg ttttgcaaga cgtaggtaaa   4260
ttgattgaag aaggcggaga ggagcctgga caccttgtgc aggaaggcat cgcagctgat   4320
gtccttggcg cagtcttgga gtggatcaga acagaaaagg gggattcctt cttgaaggag   4380
gccaagacaa gctccaatct caagttggag gatttcagac cgcagcatct taagaggtca   4440
aagttggatg ccttcatgtt gacttaa                                        4467
```

<210> SEQ ID NO 4
<211> LENGTH: 1488
<212> TYPE: PRT
<213> ORGANISM: Triticum aestivum

<400> SEQUENCE: 4

```
Met Gly His Gln Gly Gln Thr Met Met Tyr Pro Ser Val Ala His Pro
1               5                   10                  15

Ile Pro Pro Gln Leu Gly Asn Val Asn Leu Asn Met Ala Ser Gln Tyr
            20                  25                  30

Pro Gln Gln Gln Gln Asn Lys Leu Val Ala Pro Arg Lys Ser Ser Asn
        35                  40                  45

Ile Lys Ile Thr Asp Pro Asn Thr Asn Lys Glu Val Val Leu Gly Arg
    50                  55                  60

Pro Ser Pro Asn Val Ala Val Gln Pro Gln Gln Val Ser Gly Val Ala
65                  70                  75                  80

Thr Gln Pro Met Val Tyr Tyr Thr Asn Pro Gln Gln Thr Ser Tyr Asn
                85                  90                  95

Gln Ser Gly Thr Tyr Tyr Ser Gly Thr Ala Gly Val Val Pro Thr Gly
            100                 105                 110

Ser Gln Gly Arg Phe Gly Tyr Pro Ala Thr Gln Ala Gly Gln Ser Ile
        115                 120                 125

Pro Phe Met Asn Pro Ser Met Ser Asn Thr Val Pro Ala Ser His Lys
    130                 135                 140

Asp Asn Ile Ala Gly Pro Ala Pro Ser Gly Gln Ser Gln Leu Ile Gly
145                 150                 155                 160

Lys Pro Gln Gly Gly Leu His Met Glu Lys Pro Val Pro Ser Val Lys
                165                 170                 175

Ile Ser Met Pro Ala Gly Arg Ser Asp Ala Ser Lys Phe Gly Val Ala
            180                 185                 190

Asp His Ala Val Gln His Arg Gln Lys Asp Asn Glu Val Ile Ser Gly
        195                 200                 205
```

-continued

```
Ala Met Val Ser Asn Lys Pro Val Ser Glu Lys Glu Ser Lys Ala Pro
    210                 215                 220
Ser Ile Pro Glu Lys His Ser Lys Glu Ser Lys Ala Pro Ser Ala Val
225                 230                 235                 240
Glu Lys His Pro Thr Ala Val Thr Gln Pro Leu Pro Ile Gln Ala Ala
                245                 250                 255
Lys Pro Glu Thr Asp Ala Ala Thr Ala Asn Ser Pro Ser Phe Leu Thr
                260                 265                 270
Gly Ala Asp Glu Lys Lys Glu Ser Leu Pro Met Thr Asp Ser Leu Lys
            275                 280                 285
Asp Asn Lys Lys Asn Ala Thr Arg Asn Asp Thr Lys Asn Leu Pro Gln
    290                 295                 300
Gln Pro Gln Ser Ala Ser Pro Ala Glu Glu Leu Lys Gly Gln Thr Ser
305                 310                 315                 320
Val Lys Leu Gly Asp Asp Val Val Gly His Met Glu Thr Lys Ser Phe
                325                 330                 335
Asp Ser Glu Lys Val Asp Leu Thr Ser Lys Val Ser Gly Leu Thr Ser
                340                 345                 350
Ala Thr Ser Glu Ser Ser Ile Ser Pro Ile Leu Gly Lys Ser Glu Ala
            355                 360                 365
Asp Ser Thr Ser Val Asp Ala Ala Asp Val Pro Ala Met Val Ile Ser
    370                 375                 380
Ser Ala Lys Leu Ser Ser Ala Ser Thr Gly Glu Pro Gln Ala Val Glu
385                 390                 395                 400
Ser Leu Gly Val Ala Ala Val Lys Ser Lys Glu Ile Glu Ile Thr His
                405                 410                 415
Gln Ile Ser Pro Glu Ser Ser Asp Gly Lys Ile Met Ser Asp Ser Thr
                420                 425                 430
Glu Asn Glu Ser His Asp Phe Thr Val Asp Leu Ala Glu Gln Ala Ser
            435                 440                 445
Leu Ala Thr Ser Lys Pro Gly Asn Ser Asp Ala Thr Ser Phe Val Thr
    450                 455                 460
Asp Pro Gln Glu Leu Pro Lys Glu Cys Thr Thr Ser Val Pro Glu Asp
465                 470                 475                 480
His Ser Leu Met Asn Thr Ser His Asn Lys Asp Thr Gln Thr Leu Ser
                485                 490                 495
Ala Ser Val Asp Ala Ser Asp Val Ser Glu Val Asn Ser Gly Thr Ser
                500                 505                 510
Ser Glu Ser Thr Ser Gln Ser Thr Asn Asp Lys Asp Ile Arg Ser Ser
            515                 520                 525
Ile Gln Glu Thr Gly Leu Ala Val Ser Gly Ile Thr Pro Gly Met Leu
    530                 535                 540
Pro Val Asn His Ser Val Ala Ser Glu Gly Gln Val Lys His Ala Asp
545                 550                 555                 560
Gly Ala Lys Asp Glu Ser Ser Thr Glu Gln Ser Ser Ala Val Pro Thr
                565                 570                 575
Gly Ser Val Arg Pro Leu Ser Arg Glu Lys Pro Thr Ala Glu Leu Ala
                580                 585                 590
Arg Thr Lys Ser Thr Ala Gly Arg Lys Lys Arg Lys Glu Met Leu
            595                 600                 605
Ser Lys Ala Asp Ala Ala Gly Ser Ser Asp Leu Tyr Asn Ala Tyr Lys
    610                 615                 620
```

-continued

Gly Pro Gln Glu Gln Ser Glu Ser Val Ala Thr Ser Asp Gly Ala Asp
625                 630                 635                 640

Ser Ser Ser Thr Val Asp Gly Thr His Val Leu Pro Glu Glu Ser Glu
        645                 650                 655

Arg Glu Val Met Cys Glu Asp Gly Lys Lys Val Glu Pro Asp
        660                 665                 670

Asp Trp Glu Asp Ala Ala Asp Met Ser Thr Pro Lys Leu Gln Ser Ser
        675                 680                 685

Asp Ser Gly Asn Gln Ala Ser Ala Val Gln Leu Pro Asp Ser Asp Met
690                 695                 700

Thr Glu Ala Asn Gly Arg Lys Lys Tyr Ser Arg Asp Phe Leu Leu Thr
705                 710                 715                 720

Phe Ala His Gln Tyr Ser Ser Leu Pro Val Gly Ile Arg Met Asp Thr
                725                 730                 735

Val Thr Ser Thr Leu Phe Lys Asp Leu Ala Gly Lys Ser Tyr Val Ile
                740                 745                 750

Asp Arg Glu Pro His Pro Ser Ser Ala Arg Gly Ser Asp Arg Pro Thr
        755                 760                 765

Ser Arg Gly Asp Arg Arg Gly Pro Ala Met Asp Asp Lys Trp Leu
770                 775                 780

Lys Ser Gly Val Pro Tyr Ser Pro Asn Arg Asp Ala His Met Asp Leu
785                 790                 795                 800

Thr Asn Gly Pro Ala Ile Asn Tyr Arg Gly Gly Pro Gly Gly Ala His
                805                 810                 815

Gly Val Leu Arg Asn Pro Arg Gly Ala Leu Leu Val Gly Pro Gln Ser
            820                 825                 830

Asn Ala Pro Gln Val Pro Arg Ser Gly Ser Asp Ala Asp Arg Trp Gln
                835                 840                 845

Gln Lys Gly Leu Ile Pro Ser Pro Val Thr Pro Met Gln Val Met His
        850                 855                 860

Lys Ala Glu Lys Lys Tyr Val Val Gly Lys Val Ser Asp Glu Glu Gln
865                 870                 875                 880

Ala Lys Gln Arg Gln Leu Lys Ala Ile Leu Asn Lys Leu Thr Pro Gln
                885                 890                 895

Asn Phe Asp Lys Leu Phe Glu Gln Val Lys Glu Val Asn Ile Asp Asn
        900                 905                 910

Val Ser Thr Leu Thr Gly Val Ile Ser Gln Ile Phe Asp Lys Ala Leu
        915                 920                 925

Met Glu Pro Thr Phe Cys Glu Met Tyr Ala Asn Phe Cys Ser His Leu
930                 935                 940

Ala Gly Ala Leu Pro Asp Phe Ser Glu Asp Asn Glu Lys Ile Thr Phe
945                 950                 955                 960

Lys Arg Leu Leu Leu Asn Lys Cys Gln Glu Glu Phe Glu Arg Gly Glu
                965                 970                 975

Arg Glu Glu Ala Glu Ala Asp Lys Thr Glu Glu Gly Glu Ile Lys
        980                 985                 990

Gln Thr Lys Glu Glu Arg Glu Glu Lys Arg Val Lys Ala Arg Arg Arg
        995                 1000                1005

Met Leu Gly Asn Ile Arg Leu Ile Gly Glu Leu Tyr Lys Lys Arg
        1010                1015                1020

Met Leu Thr Glu Arg Ile Met His Glu Cys Ile Lys Lys Leu Leu
        1025                1030                1035

Gly Asn Tyr Gln Asn Pro Asp Glu Glu Asn Ile Glu Ala Leu Cys

```
                    1040                1045                1050
Lys  Leu  Met  Ser  Thr  Ile  Gly  Glu  Met  Ile  Asp  His  Pro  Lys  Ala
          1055                1060                1065

Lys  Glu  His  Met  Asp  Ala  Tyr  Phe  Asp  Arg  Met  Arg  Asn  Leu  Ser
          1070                1075                1080

Thr  Ser  Gln  Leu  Ile  Ser  Ser  Arg  Val  Arg  Phe  Leu  Leu  Arg  Asp
          1085                1090                1095

Ser  Ile  Asp  Leu  Arg  Lys  Asn  Lys  Trp  Gln  Gln  Arg  Arg  Lys  Val
          1100                1105                1110

Asp  Gly  Pro  Lys  Lys  Ile  Asp  Glu  Val  His  Arg  Asp  Ala  Ala  Gln
          1115                1120                1125

Glu  Arg  His  Ala  Gln  Ser  Ser  Arg  Ser  Arg  Gly  Pro  Val  Val  Ser
          1130                1135                1140

Ser  Leu  Pro  Arg  Arg  Gly  Ala  Pro  Ser  Met  Asp  Tyr  Gly  Ser  Arg
          1145                1150                1155

Gly  Ser  Ala  Ala  Pro  Leu  Val  Ser  Pro  Gly  Pro  Gln  Gln  Arg  Gly
          1160                1165                1170

Arg  Gly  Phe  Gly  Asn  Gln  Asp  Ile  Arg  Tyr  Glu  Gln  Glu  Arg  His
          1175                1180                1185

Gln  Phe  Asp  Arg  Thr  Val  Pro  Leu  Pro  Gln  Arg  Ser  Val  Lys  Asp
          1190                1195                1200

Glu  Ala  Ile  Thr  Leu  Gly  Pro  Gln  Gly  Gly  Leu  Ala  Arg  Gly  Met
          1205                1210                1215

Ser  Leu  Arg  Gly  Gln  Pro  Pro  Val  Ser  Asn  Ser  Glu  Leu  Pro  Ser
          1220                1225                1230

Val  Val  Asp  Gln  Arg  Arg  Ile  Val  Ser  Gly  Pro  Asn  Gly  Tyr  Asn
          1235                1240                1245

Ser  Val  Pro  Ser  Thr  Thr  Arg  Glu  Asp  Thr  Ser  Ser  Arg  Ile  Pro
          1250                1255                1260

Asp  Arg  Phe  Ser  Gly  Arg  Ile  Ala  Pro  Ala  Ala  Gln  Ser  Ala  Ser
          1265                1270                1275

Ser  Ser  His  Arg  Pro  Ala  Ser  Gln  Glu  Gly  Arg  Ser  Gly  Asn  Lys
          1280                1285                1290

Ser  Tyr  Ser  Glu  Glu  Glu  Leu  Arg  Glu  Lys  Ser  Ile  Ala  Thr  Ile
          1295                1300                1305

Arg  Glu  Tyr  Tyr  Ser  Ala  Lys  Asp  Glu  Lys  Glu  Val  Ala  Leu  Cys
          1310                1315                1320

Ile  Glu  Glu  Leu  Asn  Ala  Pro  Ser  Phe  Tyr  Pro  Ser  Leu  Val  Ser
          1325                1330                1335

Leu  Trp  Val  Asn  Asp  Ser  Phe  Glu  Arg  Lys  Asp  Met  Glu  Arg  Glu
          1340                1345                1350

Leu  Leu  Ala  Lys  Leu  Phe  Val  Gly  Leu  Tyr  Asn  Gly  Gly  Tyr  Asn
          1355                1360                1365

Leu  Leu  Ser  Lys  Pro  Gln  Leu  Ile  Glu  Gly  Leu  Ser  Ser  Val  Leu
          1370                1375                1380

Ala  Ser  Leu  Glu  Asp  Ala  Leu  Ser  Asp  Ser  Pro  Arg  Ala  Ala  Glu
          1385                1390                1395

Tyr  Leu  Gly  Arg  Leu  Leu  Ala  Arg  Phe  Val  Val  Glu  Lys  Ile  Leu
          1400                1405                1410

Val  Leu  Gln  Asp  Val  Gly  Lys  Leu  Ile  Glu  Glu  Gly  Gly  Glu  Glu
          1415                1420                1425

Pro  Gly  His  Leu  Val  Gln  Glu  Gly  Ile  Ala  Ala  Asp  Val  Leu  Gly
          1430                1435                1440
```

```
Ala Val Leu Glu Trp Ile Arg Thr Glu Lys Gly Asp Ser Phe Leu
    1445            1450            1455

Lys Glu Ala Lys Thr Ser Ser Asn Leu Lys Leu Glu Asp Phe Arg
    1460            1465            1470

Pro Gln His Leu Lys Arg Ser Lys Leu Asp Ala Phe Met Leu Thr
    1475            1480            1485

<210> SEQ ID NO 5
<211> LENGTH: 28
<212> TYPE: DNA
<213> ORGANISM: Artificial Sequence
<220> FEATURE:
<223> OTHER INFORMATION: Primer used to amplify a fragment of
      eIF(iso)4E-2

<400> SEQUENCE: 5
cacccgcaaa tggaggcaaa tggactgt                                      28

<210> SEQ ID NO 6
<211> LENGTH: 24
<212> TYPE: DNA
<213> ORGANISM: Artificial Sequence
<220> FEATURE:
<223> OTHER INFORMATION: Primer used to amplify a fragment of
      eIF(iso)4E-2

<400> SEQUENCE: 6
tccacctctg cttggtttct gact                                          24

<210> SEQ ID NO 7
<211> LENGTH: 28
<212> TYPE: DNA
<213> ORGANISM: Artificial Sequence
<220> FEATURE:
<223> OTHER INFORMATION: primer used to amplify a fragment of eIF4G

<400> SEQUENCE: 7
cacctcagca gcaccattgg tatctcca                                      28

<210> SEQ ID NO 8
<211> LENGTH: 23
<212> TYPE: DNA
<213> ORGANISM: Artificial Sequence
<220> FEATURE:
<223> OTHER INFORMATION: primer used to amplify a fragment of eIF4G

<400> SEQUENCE: 8
gctcggagca ttcaactcct caa                                           23
```